United States Patent
McPhillips

(10) Patent No.: US 7,303,670 B2
(45) Date of Patent: Dec. 4, 2007

(54) COMPOSITIONS, DEVICES, AND METHODS FOR USE IN ENVIRONMENT REMEDIATION

(75) Inventor: Kevin McPhillips, Arbuckle, CA (US)

(73) Assignee: R. H. Dyck. Inc., Woodland, CA (US)

( * ) Notice: Subject to any disclaimer, the term of this patent is extended or adjusted under 35 U.S.C. 154(b) by 0 days.

(21) Appl. No.: 11/178,636

(22) Filed: Jul. 11, 2005

(65) Prior Publication Data

US 2006/0032804 A1 Feb. 16, 2006

Related U.S. Application Data

(63) Continuation-in-part of application No. 10/992,296, filed on Nov. 18, 2004.

(60) Provisional application No. 60/539,406, filed on Jan. 27, 2004.

(51) Int. Cl.
*C02F 1/52* (2006.01)

(52) U.S. Cl. ............... 210/170.03; 210/209; 210/505; 210/508; 210/728; 210/747

(58) Field of Classification Search ............... 210/702, 210/723, 728, 747, 170.01, 170.03, 209, 210/503, 504, 505, 506, 508

See application file for complete search history.

(56) References Cited

U.S. PATENT DOCUMENTS

| | | | |
|---|---|---|---|
| 3,865,728 A | 2/1975 | Abbott et al. | |
| 4,476,185 A | 10/1984 | Spittle | 428/290 |
| 5,006,267 A | 4/1991 | Vaughn et al. | |
| 5,281,338 A * | 1/1994 | Harris et al. | 210/691 |
| 5,338,131 A | 8/1994 | Bestmann | 405/24 |
| 5,425,597 A | 6/1995 | Bestmann | 405/24 |
| 5,468,536 A | 11/1995 | Whitcomb et al. | |
| 5,641,244 A | 6/1997 | Bestmann | 405/16 |
| 5,651,641 A | 7/1997 | Stephens et al. | 405/302.6 |
| 5,678,954 A | 10/1997 | Bestmann | 405/24 |
| 5,741,832 A | 4/1998 | Spittle | 523/132 |
| 5,779,782 A | 7/1998 | Spittle | 106/164.3 |
| 5,916,027 A | 6/1999 | Spittle | 47/9 |
| 5,942,029 A | 8/1999 | Spittle | 106/164.3 |
| 6,076,299 A | 6/2000 | Spittle et al. | 47/9 |
| 6,158,167 A | 12/2000 | Spittle | 47/9 |
| 6,182,834 B1 | 2/2001 | Kim et al. | |
| 6,349,499 B1 | 2/2002 | Spittle | 47/9 |
| 6,360,478 B1 | 3/2002 | Spittle | 47/9 |
| 6,419,839 B1 | 7/2002 | Cox et al. | |
| 6,447,677 B2 | 9/2002 | King | |
| 6,527,477 B1 | 3/2003 | Allard | 405/45 |
| 6,547,493 B2 | 4/2003 | Spangler et al. | 405/302.6 |
| 6,592,295 B2 | 7/2003 | McPhillips | 405/129.9 |
| 6,663,324 B2 | 12/2003 | Nordloh | 405/302.6 |
| 6,729,807 B1 | 5/2004 | Spittle | 405/302.7 |
| 6,749,748 B1 * | 6/2004 | Macpherson et al. | 210/206 |
| 6,929,425 B1 | 8/2005 | Kimberlin et al. | |
| 7,067,056 B2 | 6/2006 | Collins | |
| 2001/0053545 A1 | 12/2001 | Engwer | |

(Continued)

*Primary Examiner*—Christopher Upton
(74) *Attorney, Agent, or Firm*—Fliesler Meyer LLP

(57) ABSTRACT

What is disclosed are compositions, devices, and methods for use in environmental remediation. The compositions are for use in a variety of environmental remediation barriers including fiber rolls, blankets, and berms. Applications for the use of the compositions, devices, and methods include remediation of runoff water, of livestock waste, of eutrification of waterways, and for the revetment of banks.

11 Claims, 10 Drawing Sheets

U.S. PATENT DOCUMENTS

| | | |
|---|---|---|
| 2002/0008071 A1 | 1/2002 | Chinn |
| 2002/0043493 A1 | 4/2002 | Patil |
| 2002/0043496 A1* | 4/2002 | Boddu et al. ............... 210/504 |
| 2002/0131827 A1 | 9/2002 | Spangler et al. |
| 2002/0155237 A1 | 10/2002 | Allard |
| 2003/0031511 A1 | 2/2003 | Tyler |
| 2004/0055939 A1 | 3/2004 | Wybo |
| 2004/0074271 A1* | 4/2004 | Krysiak et al. ................ 71/27 |
| 2004/0091326 A1 | 5/2004 | Spittle |
| 2004/0202851 A1* | 10/2004 | Goodrum et al. ........... 428/220 |
| 2004/0262225 A1* | 12/2004 | C. et al. ..................... 210/691 |
| 2005/0254899 A1 | 11/2005 | Tyler |

* cited by examiner

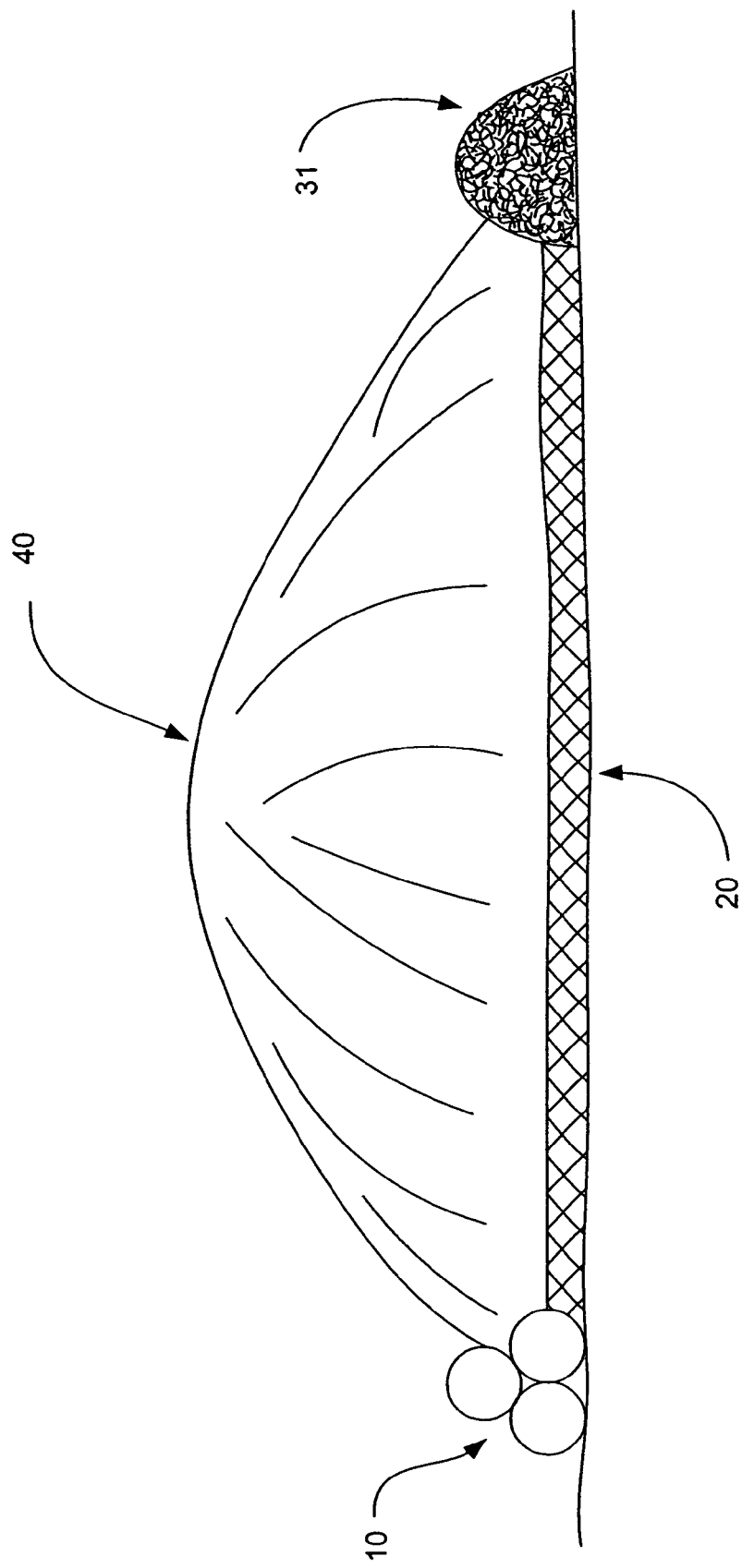

COMPOSITIONS, DEVICES, AND METHODS FOR USE IN ENVIRONMENT REMEDIATION

CLAIM TO PRIORITY

The present application claims the benefit of priority and is a continuation-in-part of U.S. patent application Ser. No. 10/992,296, entitled "COMPOSITIONS, DEVICES, AND METHODS FOR USE IN ENVIRONMENTAL REMEDIATION", inventor: Kevin McPhillips, filed: Nov. 18, 2004, which claims priority under 35 U.S.C. § 119(e) to U.S. Provisional Patent Application No. 60/539,406, entitled "COMPOSITIONS, DEVICES, AND METHODS FOR USE IN ENVIRONMENTAL REMEDIATION", filed: Jan. 27, 2004. These applications are incorporated herein by reference.

FIELD OF THE ART

The field of art disclosed herein pertains to compositions, devices, and methods suited for a variety of applications in environmental remediation.

BACKGROUND

The uses of structural barriers for a variety of applications in environmental remediation are generally well described. Several types of Environmental Remediation Barriers (ERBs) are used in earth and hydraulic engineering, such exemplary structures including fiber rolls, mats, blankets, and berms. Originally, major applications of ERBs included erosion and sedimentation control, revegetation, and revetment. More recently, the potential for such structures to serve additionally in the capacity of removal of natural and manmade pollutants from residential, industrial, and agricultural sources, and remediation of eutrification has been described.

As the name of one type of ERB, fiber roll, suggests, ERBs packed into a covering, such as a netted material, may be filled with fibers; typically a single natural fiber such as abaca, hemp, jute, flax, sisal, coir, or straw materials. For a major application of fiber-filled ERBs in erosion and sediment control, the purpose of the fiber filling is primarily structural. In that regard, though the natural fibers described are capable of absorbing water, one necessary attribute of the fiber filler has been to provide an effective porosity once packed that allows for the ready passage of water, while promoting the retention of mud, sediment, gravel, and the like. Other desirable attributes of natural fibers used in ERBs include ready availability in high volume and low cost, requirement to be germ, insect and weed free, free of chemical pollutants, ability to degrade after use; thereby obviating creation of harmful waste, and ease of processing into targeted devices.

Materials in addition to natural fibers have been suggested as supplemental constituents in ERBs. Particularly, vegetative matter, as well as nutrients and fertilizers for revegetation and revetment have been described. Materials that have been suggested include sawdust, wood chips, bark, compost, flocculants, water absorbents, and pesticides. A major objective in the field has been to establish environmental remediation practices that are consistent with good practices for environmental protection in general. In that regard, the reuse of natural materials, such as saw dust, wood chips, bark, and compost, that would otherwise go to waste has been a motive for creating fillings for ERBs.

Especially in consideration of the use of ERBs in functions where the filling has a requirement that is more than structural; moreover where the filling must perform additional multiple functions, such as clarification of runoff water and removal of pollutants, the targeted and judicious selection of materials tailored for such multifunctional use throughout the lifetime of the ERBs still remains a challenge. Accordingly, a need exists for more effective compositions of materials that are multifunctional for a variety of environmental remediation needs, and for a range of ERBs utilizing such compositions and their use.

BRIEF DESCRIPTION OF DRAWINGS

FIG. 4b; is a cross section through a manure pile depicting the of the use of fiber rolls, blankets, and berms for remediation of livestock waste FIG. 5; is a depiction of the use of fiber rolls, blankets, and berms for remediation of storm water runoff.

DETAILED DESCRIPTION

Figure 1:
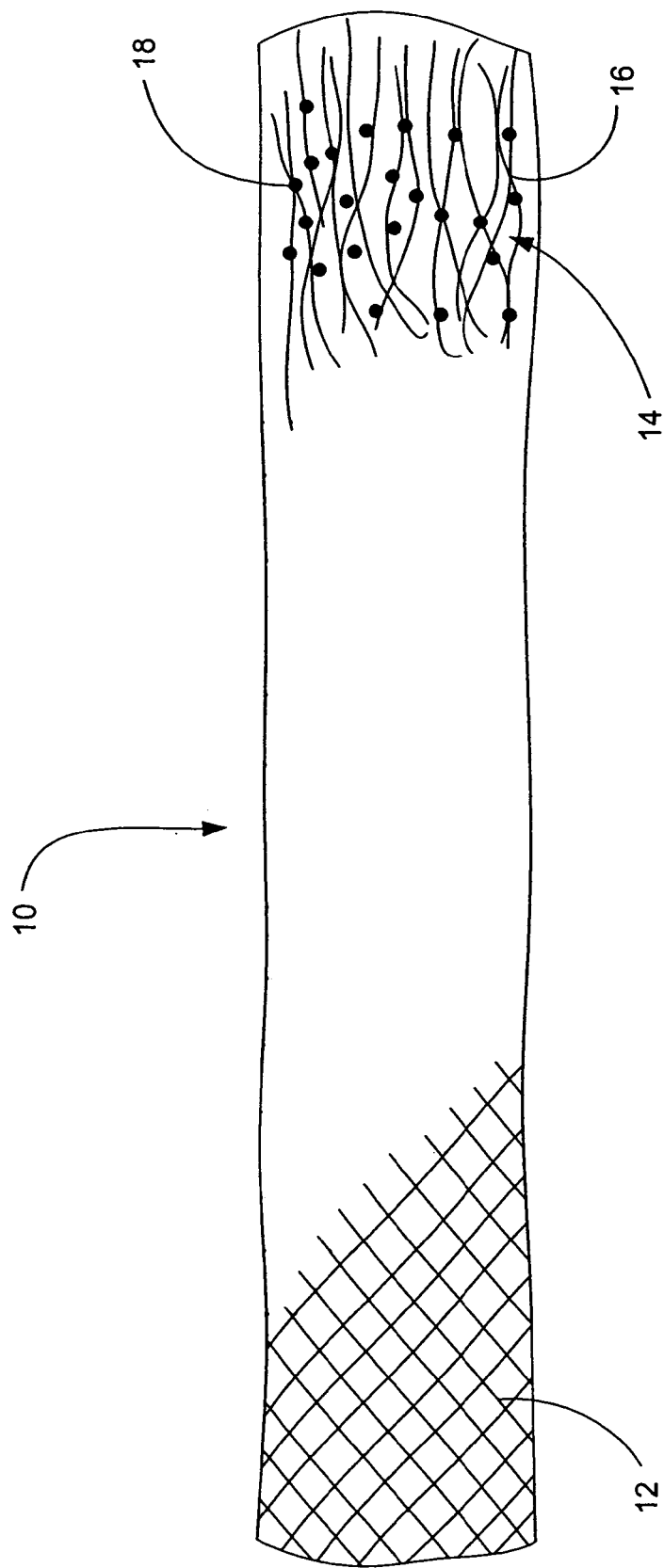
FIG. 1; is a side view of a fiber roll.

What will be described and disclosed herein in connection with certain embodiments and procedures is not intended to be limited to the embodiments shown, but is to be accorded the widest scope consistent with the principles and features disclosed. Thus, the intent is to cover all such alternatives, modifications, and equivalents that fall within the spirit and scope of what is presently disclosed as defined by the appended claims.

In this specification and in the claims that follow, reference will be made to a number of terms that shall be defined to have the following meaning:

The term "fiber" has a number of common meanings which include: (1) course indigestible plant matter, consisting primarily of polysaccharides, such as cellulose; and (2) natural or synthetic filaments, e.g. cotton or nylon, and materials made from such filaments. The use of the term "fiber" herein includes both of these definitions. Materials made from natural fibers include materials that are polysaccharide in nature, e.g. cotton or linen, or polypeptide in nature, e.g. wool or silk. Natural fibers containing significant cellulose content are of particular interest to the subject of what is disclosed herein. The broad class of natural cellulose-containing fiber materials includes such examples as flax, jute, sisal, coir, kenaf, ramie, cotton, bagasse, hemp, rice straw, wheat straw, barley straw, and oat straw. These exemplary natural fibers vary considerably in their cellulose fiber content. For example, cotton is composed of 98% cellulose, while bagasse is composed of 50% cellulose, 25% pentosan and 25% lignin. Cotton is an unusual example of a natural fiber material that is almost completely cellulose, and bagasse is more typical. In order to make materials that have a higher cellulose fiber content, significant processing is generally required. Cotton, linen, paper, cardboard, and paperboard are examples of materials that are manufactured from processed cellulose. Finally, there are several large classes of synthetic fibers, containing a plurality of members having homologous basic structures that are varied to give different properties. Some examples of classes of synthetic fiber materials include polyamides, polyacrylates, polyesters, and polyacrylamides. Such synthetic fiber materials are made from starting materials that are also synthetic. An interesting type of synthetic fiber includes natural fibers used as starting materials that are chemically modified into man-made fibers. One relevant example of such a class are cellulosics, of which rayon, and cellulose acetate are exemplary.

The term "environmental remediation barrier" is used herein to refer to fiber rolls, mats and blankets, and berms. Fiber rolls, also referred to as wattles or fiber logs, are elongate rolls of a natural fiber material contained in a covering, having diameters of about 6-24 inches and 4-25 feet in length. When they are used in the capacity of erosion control, they are typically used along the top, face, and grade breaks of exposed and erodible slopes. Blankets and mats, more commonly known as rolled erosion control products, are commonly used for the short term stabilization of disturbed soil areas such as steep slopes, slopes where erosion hazard is high, slopes where mulch must be anchored, disturbed areas where plants are slow to develop, channels where flow velocities exceed 1.0 m/s, and in channels to be vegetated. As the name suggests, the basic structure of blankets and mats is sheet. Sizes and dimensions of mats and blankets vary tremendously, depending on the application. Some typical dimensions are lengths of about 67 feet to 112 feet, widths of about 4 to 16 feet and thickness of about 0.35 to 0.90 inches. Mats and blankets can be rolled and bundled to produce structures similar in shape to fiber rolls, and used in a similar capacity. Berms may be either of the bag-type, or created on-site, typically by pneumatic application, and are used in the same way that fiber rolls are used. Standard dimensions of bag berms are 1.5 feet long, 1 foot wide, and 3 inches thick, and for use in erosion control are typically filled with gravel, and the like. While those of ordinary skill in the art recognize the use of these structures in earth and hydraulic engineering applications, it is to be understood that the disclosed compositions are useful beyond the above-described ERBs.

The term aqueous run-off material is used to describe the particles that are to be removed from the water during the remediation process. The run-off material may be dissolved, colloidally suspended, non-colloidally suspended or otherwise dispersed in the water.

The term remediation process refers to the treatment of aqueous run-off material such that the run-off material is isolated or separated from the water. In addition, the remediation process refers to the retention of the sediment.

The term "aggregation" refers to the process in which material colloidally suspended becomes destabilized, thereby forming larger associations of particles. These larger associations of particles are referred to as aggregates. The terms "coagulation" and "flocculation" are sometimes used interchangeably to describe the process of formation of aggregates. The terms "coagulant" and "flocculant" are used to describe agents promoting aggregation in solution, and have been used notably in the discussion of treatment of water and wastewater. Coagulation is the clumping together of fine particles into larger particles, caused by the use of chemicals. Flocculation is the combination, agglomeration, aggregation or coagulation of suspended particles in such a way that they form small clumps or tufts (called floc). Here, the term "aggregation" is used to denote both "coagulation" and "flocculation". The term "aggregating agent" refers to a wide range of constituents that act to promote aggregation, and occur in a wide variety of classes of materials including, polymers, minerals, clays, and inorganics. Examples of aggregating agents meeting the attributes required for use in the disclosed compositions include: (1) polymers; exemplary polymers are taken from the groups of polyacrylamides, polyamines, polydadmacs, chitosans; (2) minerals such as gypsum and calcite; (3) clays such as bentonite and talc; and (4) inorganics such as polyaluminum and polyferric salts.

One aspect of a coagulation and/or flocculation agent is its capacity to coagulate and/or flocculate agents in water. In order to increase the surface area of coagulation and/or flocculation agents, these agents are preferably made up of particles of less than 10 mm in diameter. Coagulation and/or flocculation agents include for example, aquatic shells and the exoskeleton of anthropods. The coagulation and flocculation agents can function as highly absorptive or adsorptive material. The coagulation and flocculation agents can interact with material in the water either via formation of chemical and/or physical bonds. The action of an aggregating agent and the fiber material can be improved through the use of a binding agent.

The term binding agent refers to any material, which can be used to chemically or physically bind the fiber material with the coagulation and/or flocculation agent. An example of a binding agent would be a silicone rubber elastomer used to bind a crystalline polymer to a fiber material. As described, binding agents can be used to bind the coaggulation and/or flocculation agents to the fiber material.

The term polymer materials refers to both natural polymer materials including chitin, chitosan, conchiolin and synthetic polmers such as polyacrylamide, polyamine and polydadmac. Synthetic polymers include organic polymers, inorganic polymers and mixtures thereof including inorganic fillers of organic polymers and organic fillers of inorganic polymers.

The term polymer material in crystalline form refers to any polymer material in which more than 60% by weight of the polymer molecules are arranged in a regular order and pattern. e.g., polypropylene, syndiotactic polystyrene, nylon, kelvar, nomex, polyketones and polyarylate liquid crystalline polymer.

The term "adsorption" refers to the accumulation of gases, liquids, or solids on the surface of a solid or liquid. In contrast, though in the same context, "absorption" is generally defined as the uniform uptake of gases and liquids throughout a solid material. Both processes are important in the removal of pollutants in the environment, and it is to be recognized that many materials may act in both capacities. The term "adsorbent" is used for materials in the described compositions selected to adsorb pollutants of the targeted applications, though it is understood that such materials may also act to absorb the same or other species. Similarly, the term "absorbent" is used for materials of the described compositions selected to absorb undesirable bulk materials of the targeted applications, though it is understood that such materials may adsorb the same or other species.

Adsorbents meeting the attributes required for use in the described compositions occur in a wide variety of classes of materials including perlites, zeolites, clays, and carbonaceous adsorbents. Given the complexity of these materials, there are many forms and variations of materials in each class. Perlite is a generic term for a natural glass material, characterized by having, good insulating properties, light weight, neutral pH, and good adsorption properties for a wide range of chemical species; most notably organic. Zeolites are naturally occurring minerals classified in the silicate family. They are characterized by the openness of their structure that permits large ions and molecules to diffuse into their structure. Their channel sizes control the size of molecule that can pass through, and so they act as a chemical sieve. They have proven effective in removing numerous alkali, alkali earth, and transition metal ions, as well as ammonia from water. As previously mentioned, clays are naturally occurring complex minerals within the phyllosilicate group. Given their chemical structures, many types of clay are also highly effective adsorbents of a broad range of chemical species. Examples of clays that are excellent adsorbents include vermiculite and organoclay. Carbonaceous adsorbents are a diverse group of adsorbents ranging from activated charcoal, created from natural sources, such as wood, to carbonized adsorbents formed from the pyrolysis of synthetic organic materials. Aquatic mollusc shells include marine bivalves (e.g., oyster, mussel, clam, cockels, shipworms, scallop), monovalve gastrapods (limpets, snails) and cephalapoda (cuttlefish) shells. The exoskeletons of anthropods include scorpion, grasshopper, termite, cicada, moth, prawn, shrimp, lobster and crayfish shells.

One aspect of absorbents is their capacity for uptake of a liquid. It is desirable for this application that the adsorbent take up a significant volume of bulk liquid, without significant change in packed volume. Additionally, it is desirable for the adsorbent to be readily disposed of without creating environmental contamination or high cost. Materials meeting the above criteria are frequently material composites with significant portions of natural materials. Absorbents meeting the attributes required for use in the described compositions include peat-based, cotton fiber-based, bagasse-based, and urethane-based absorbents.

Figure 2:
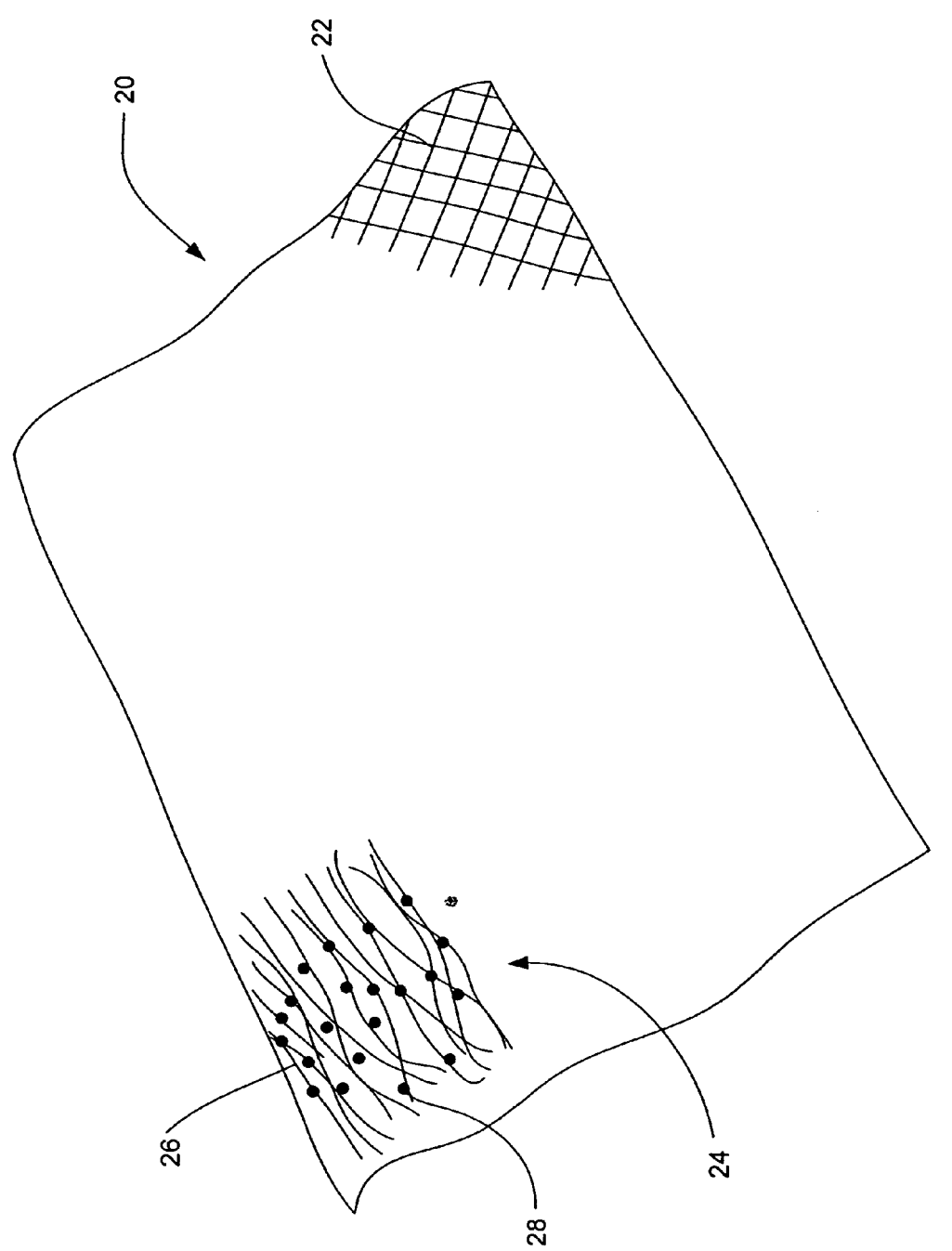
FIG. 2; is a top view of a blanket.
Figure 3A:
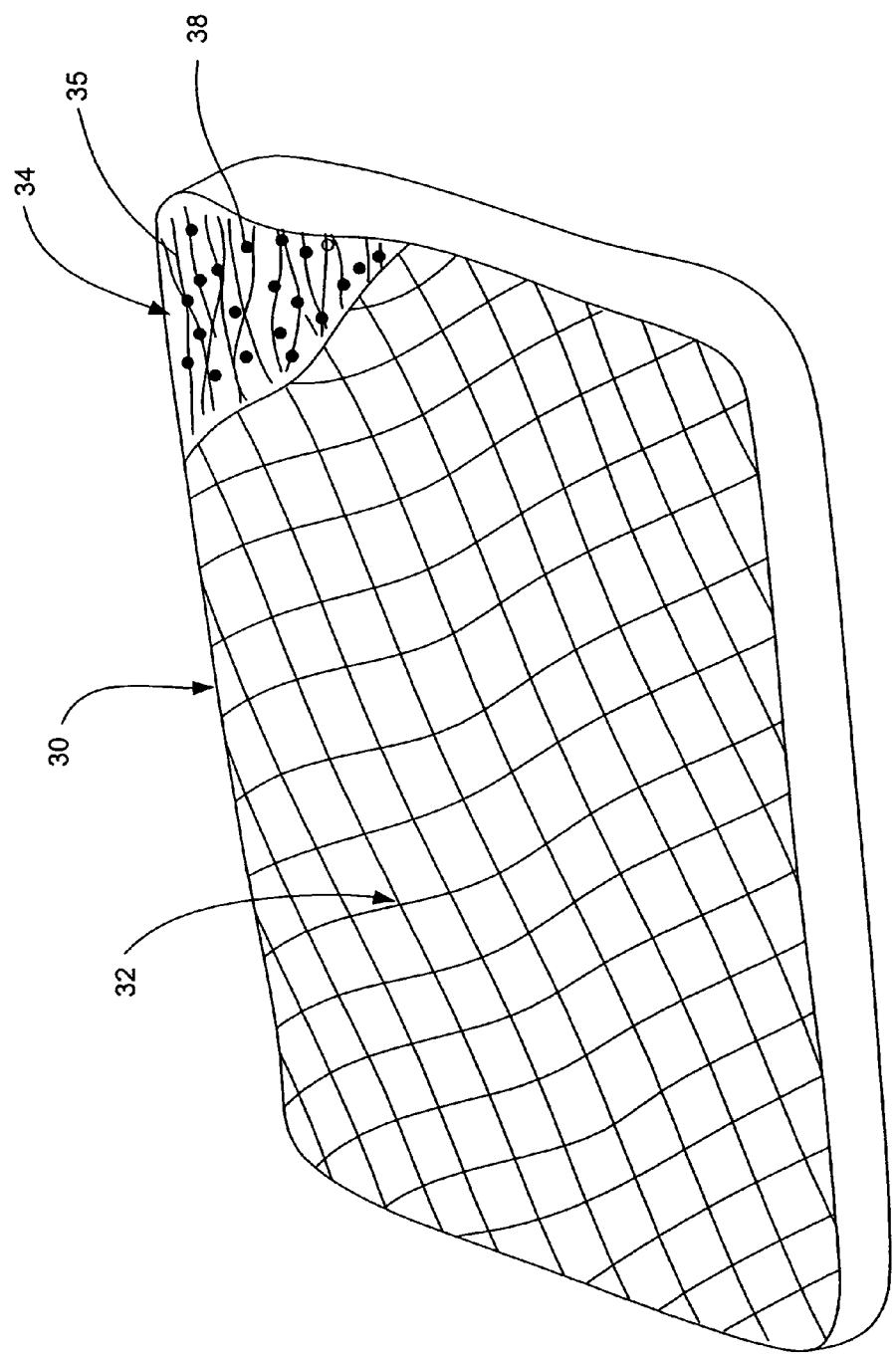
FIG. 3a; is a front view of a bag berm.
Figure 3B:
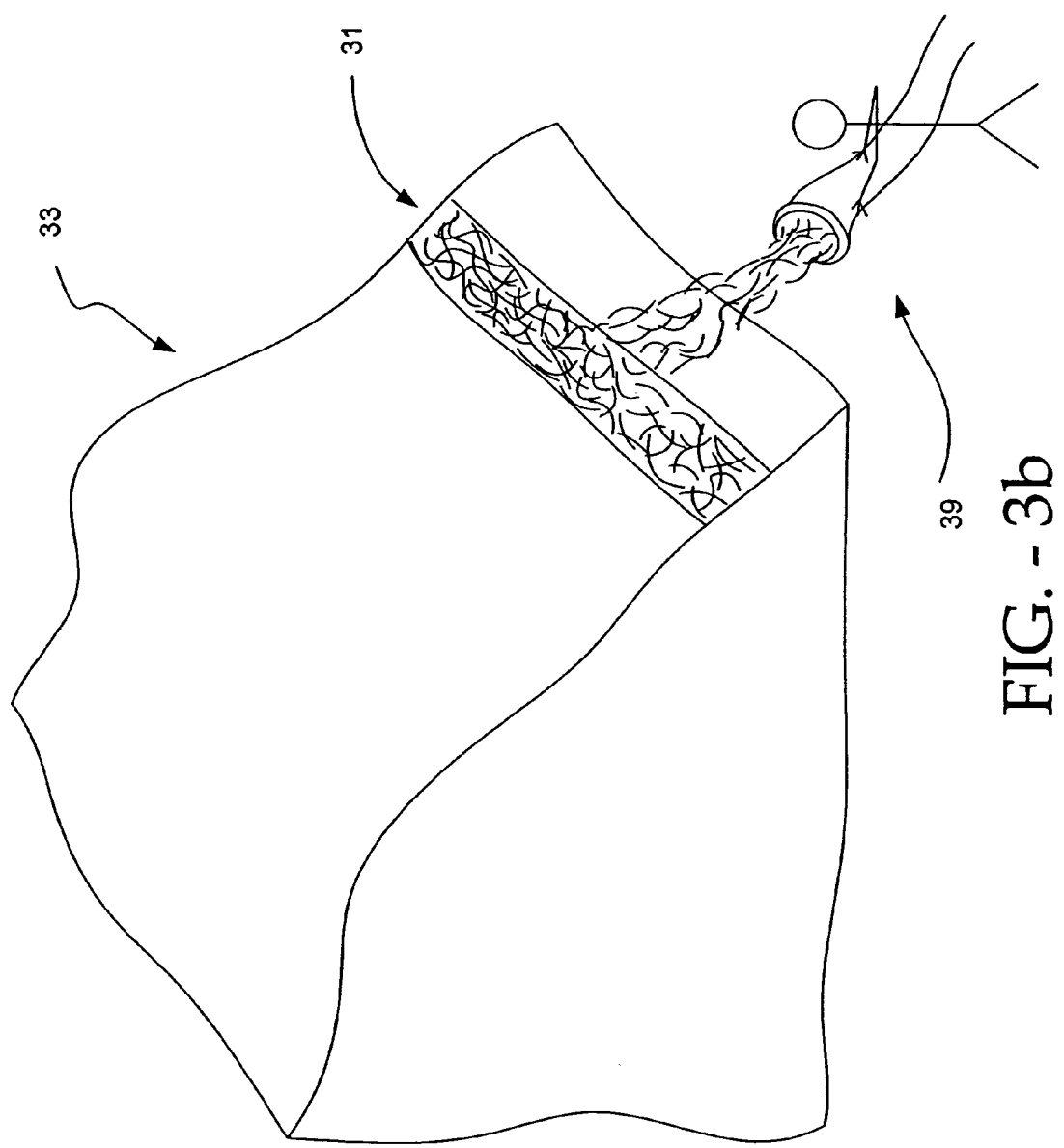
FIG. 3b; is a depiction of the pneumatic application of a composition to create a berm.

Referring now to FIG. 1-3, exemplary environmental remediation barriers are shown. In FIG. 1 the side view of a fiber roll 10 is illustrated as being uniformly tubular, and therefore of circular cross-section. The fiber roll 10 is composed of netted material 12 surrounding a filling 14. In the filling 14, two forms of constituents of the disclosed composition are illustrated; fiber 16, and particle 18. FIG. 2 shows an ERB in the form of a mat or blanket 20 with netted material 22, a filling 24, illustrating fiber 26 and particle 28 forms of the constituents of the disclosed composition. In FIGS. 3a and 3b, different types of berms are shown. In FIG. 3a, a bag berm 30 is shown, having a covering 32 of a cloth, and a filling 34, illustrating fiber 36 and particle 38 forms of the constituents of the disclosed composition. FIG. 3b illustrates the on-site creation of a berm 31 on hillside 33 through the use pneumatic application of filling 34.

As will be appreciated by those of skill in the art, ERBS contained in coverings, such as fiber roll 10, mat or blanket 20, and bag berm 30 can take on a plurality of shapes and aspect ratios that may be useful for the functions served. For example, the fiber roll 10 can be tubular with an oval, square, rectangular, ovoid or other dimensioned cross-section. Likewise, mats and blankets 20, and bag berms 30 need not be square, and may take on a variety of aspect ratios. Additionally, mats and blankets may be further bundled into rolls, giving them the flexibility of any of the uses of a fiber roll. Suitable coverings for ERBs include loosely woven fabric or netted materials made from biodegradable or photodegradable materials, or mixtures thereof that enable fluid passage as required for the particular composition and intended environmental application. Suitable biodegradable covering materials include jute, sisal, coir, suitable bast (i.e., flax) material, or combinations thereof. Suitable photodegradable covering materials include polyethylenes, polypropylenes, and polyacetates, or combinations thereof. As will be appreciated by those skilled in the art, suitable covering material will depend upon the environmental application of the compositions, and ERBs.

Figure 4A:
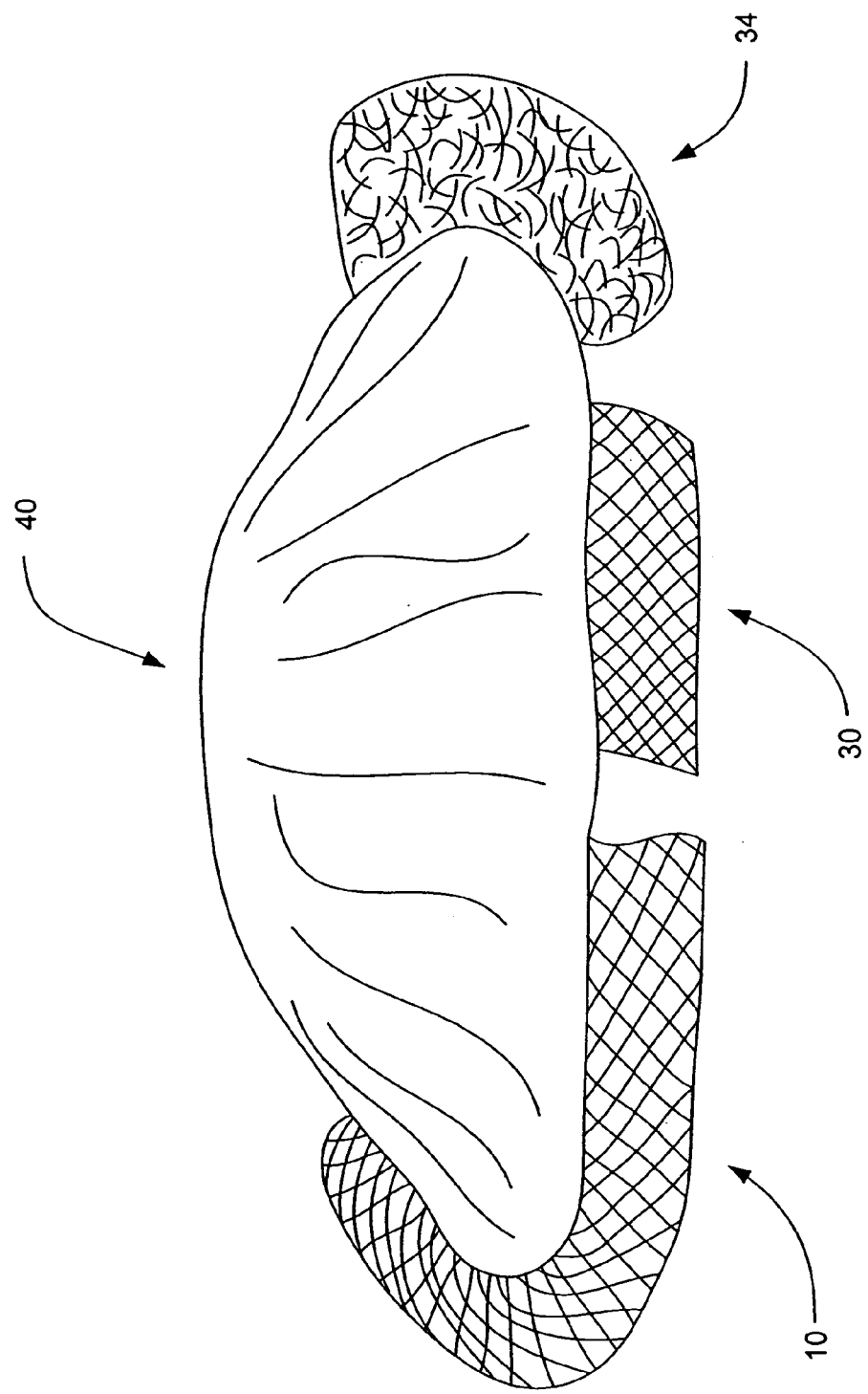
FIG. 4a; is a side view of the use of environmental remediation barriers for remediation of livestock waste.

Turning now to FIGS. 4a and 4b illustrate the use of the disclosed compositions in ERBs used in the remediation of livestock waste. In FIG. 4a, a side view of fiber roll 10, a bag berm 30, and a berm created on-site 31, surrounding a manure pile 40. In FIG. 4b, a cross section through the manure pile 40 resting on blanket 20, and surrounded by fiber roll 10 and berm created on-site 31. In this application it is desirable to adsorb ammonia; the volatilization of which creates serious odor problems, and absorb urine within the manure to prevent these constituents from being leached from the pile. In constructing the manure pile site, a blanket can be placed on the ground below the manure, while fiber rolls or berms surround the pile to prevent ammonia and urine from running off or leaching into the soil. It is contemplated that blankets can be interspersed in the manure pile as it is built, and eventually act to cover a completed pile. Such use of additional blankets acts to enhance absorption and/or degradation of the manure, if desired. A blanket can be placed initially, with manure layered over the blanket, and successive layers of blankets and manure stacked to build a layered pile. If desired, an absorbent, biodegradable paper can be used to contain the pile once the pile has reached a desired height. The absorbent, biodegradable paper can also be layered among the layers of blankets and manure. Further, shredded paper can be used with or without straw or other fiber around the base of the pile to enhance absorption and structural integrity of the pile. Similarly, stacks and rows of fiber rolls or sequential rows of berms can be used to treat runoff from a manure pile and to add structural integrity to the pile.

An embodiment of the composition for the application of FIGS. 4a and 4b used as the fillings 14, 24, and 34, of the fiber roll 10, blanket 20, and bag berm 30 respectively, as well as berm created on-site 31, is comprised of the natural fiber, rice straw, the processed fiber, carbon impregnated paper for removal of ammonia, and additional adsorbents vermiculite or perlite or a combination thereof, to enhance the selectivity and capacity for removal of the targeted substances into the ERBs as they leach from the waste pile. Additional materials extending the function of the composition can be added and include suitable aggregation agents or absorbents, or combinations thereof. An exemplary covering material for this application is biodegradable or photodegradable, as described above. As will be appreciated by those of skill in the art, while this embodiment is described in terms of manure and stockyards, other types of excrement can be treated using the described composition of this type without departing from the scope of this disclosure.

Figure 5:
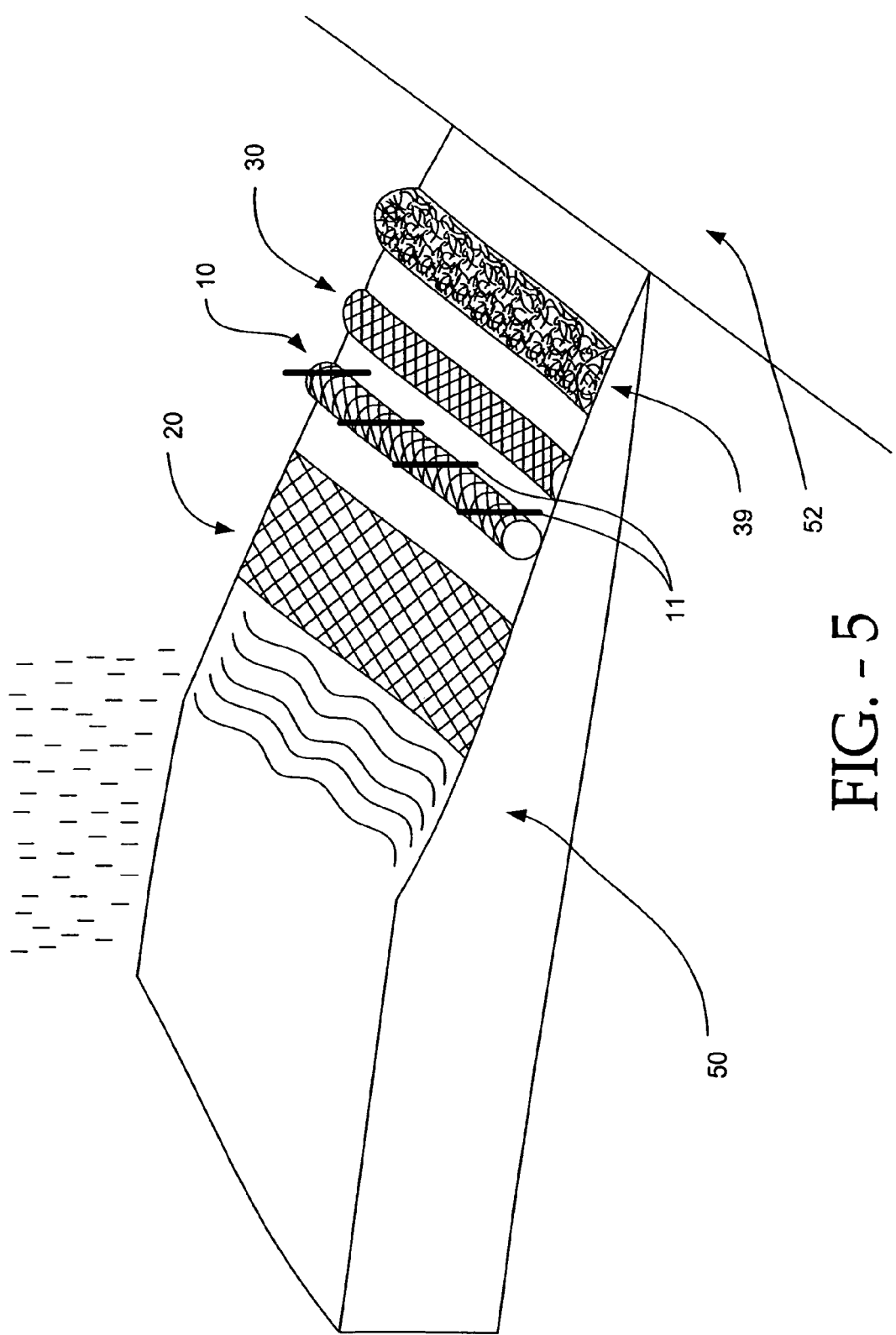

FIG. 5 illustrates a variety of ERBs that may utilize the disclosed composition in erosion control, sediment control, and additionally for treatment of storm water runoff. Hillside 50 sloping towards roadway 52 create the conditions for runoff 54. Such runoff may not only erode the hillside, carrying with it valuable topsoil, but may carry with it additionally a variety of manmade pollutants, e.g. pesticides, herbicides, fertilizers, and nutrients, as well as natural substances, such as humic acid, fulvic acid, tannic acid, and humin, potentially problematic as pollutants. Environmental remediation barriers that are useful for multifunctional purposes, including the treatment of storm water runoff are blankets 20, fiber rolls 10, bag berms 30, and berms created on-site 31. The installation of ERBs is well described, for instance in *Construction Storm Water Pollution Bulletin*, 4(11), 2000; a publication by the California Transit Authority. For fiber rolls, stakes 11 are used to keep the fiber roll barrier in place. Though shown on a hillside setting, the composition of this application is designed to treat runoff from a variety of surfaces, such as asphalt or concrete in a variety of residential, industrial, recreational, and agricultural settings.

An embodiment of the disclosed composition for the application of FIG. 5 used as the fillings 14, 24, and 34, of the fiber roll 10, blanket 20, and bag berm 30 respectively, as well as berm created on-site 31, is comprised of the natural fiber, rice straw, coir, the processed fiber, carbon impregnated paper for removal of pollutants, and additionally aggregating agents, gypsum and polyacrylamide. Vermiculite or perlite, or combinations thereof may be added to enhance the selectivity and capacity for removal of the targeted substances. Other materials extending the function of the composition can be added and include additional aggregation agents, adsorbents, or absorbents, or combinations thereof. An exemplary covering material for this application is photodegradable, as previously described. As will be appreciated by those of skill in the art, while this embodiment is described in terms of multifunctional application for environmental remediation of a hillside, other types of surfaces found in residential, industrial, recreational, and agricultural settings can be treated using a composition of this type without departing from the scope of this disclosure. For instance, the disclosed compositions of this embodiment can be used in conjunction with surfaces additionally contaminated with hydrocarbon accumulation, such as parking lots or roadways.

Figure 6A:
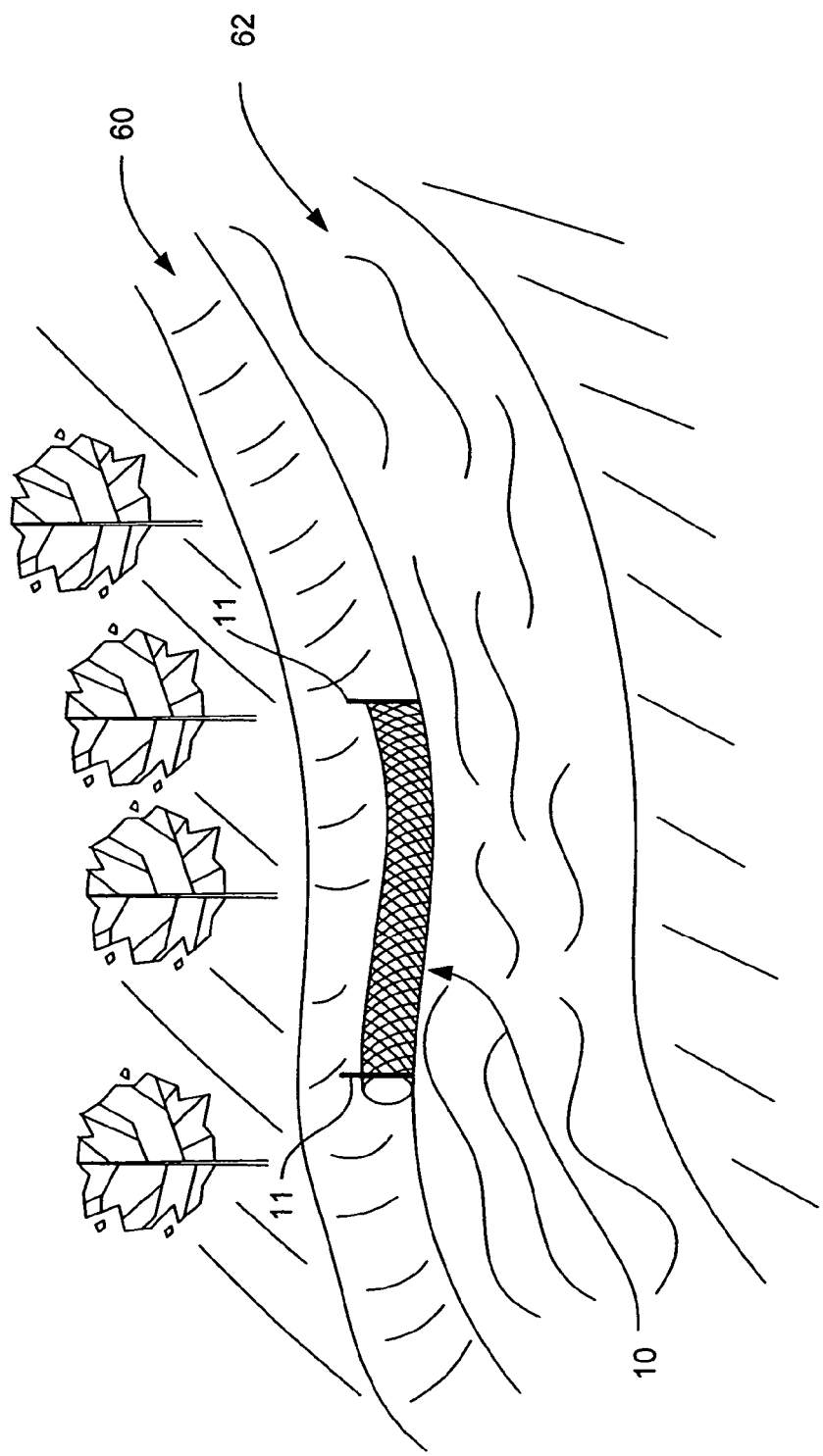
FIG. 6a; is the depiction of the use of a fiber roll for the revetment and remediation of eutrification of waterways.
Figure 6B:
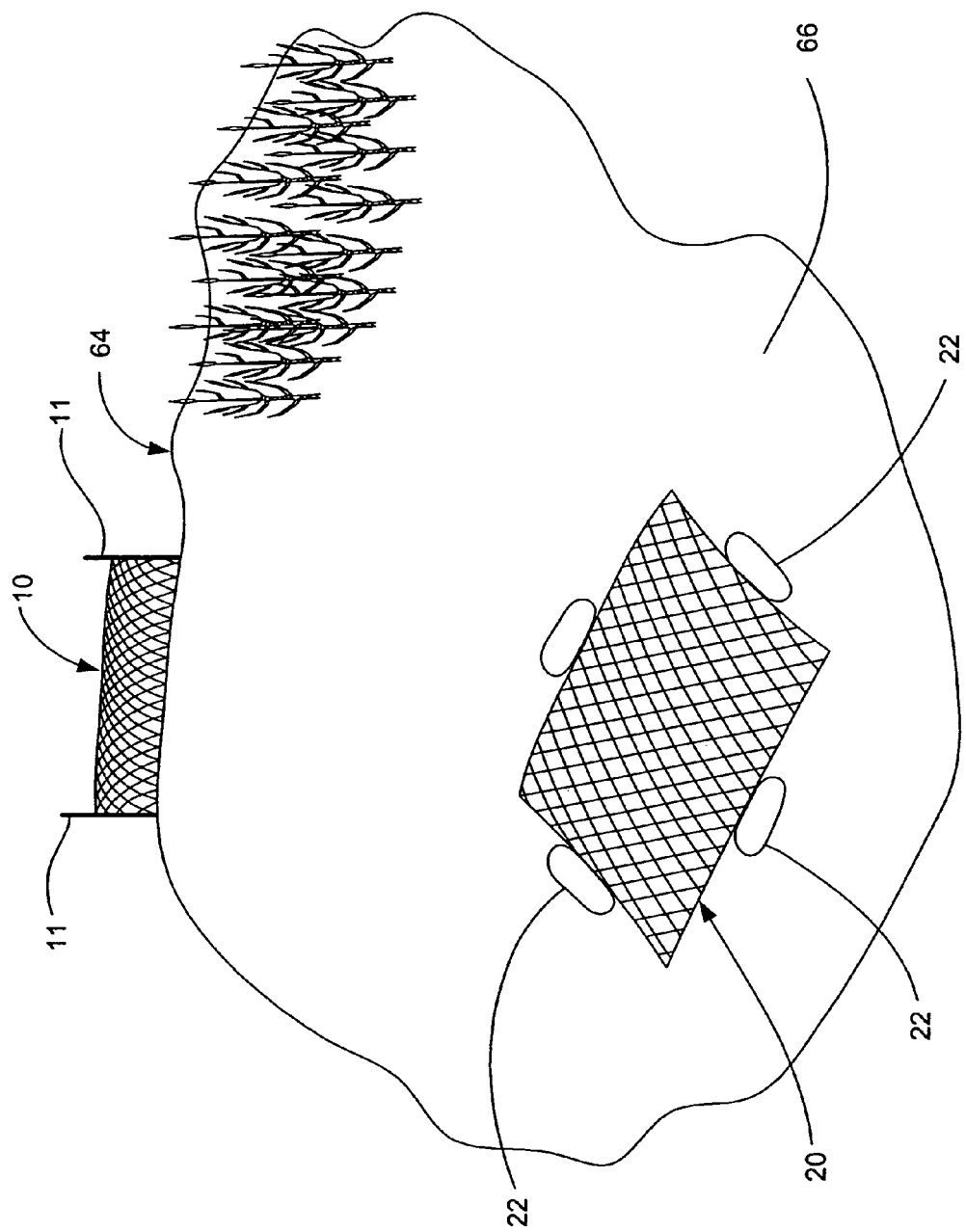
FIG. 6b; is the top view of a pond demonstrating the use of a blanket for remediation of eutrification in a pond.

In reference to FIGS. 6a and 6b, ERBs utilizing the disclosed composition in the environmental remediation of waterways are illustrated. In this application, multifunctional purposes in addition to those mentioned in the above exemplary applications would be revetment of banks and remediation of eutrification, e.g. for pond or lake clarification of algae. In FIG. 6a, a fiber roll 10 is shown installed with stakes 11, as previously described, in order to support sloping bank 60, in continuous contact with river, 62. Similarly, in FIG. 6b, fiber roll 10 is installed using stakes 11 to support shore 64 of lake 66. Additionally, blanket 20 is shown disposed on lake 66, installed with floatation devices 22. As will be described in more detail, blanket 20 in FIG. 6b is used for remediation of eutrification of ponds, lakes, streams, and the like.

In the application illustrated in FIGS. 6a and 6b, an embodiment of the composition utilizes a combination of natural fibers, flax and barley straw, and the natural fiber, paper. For uses associated with semi-aquatic communities, such as the application of environmental remediation of a riparian community or stream or lake bank, suitable filling also includes kenaf and ramie. Depending on the application and type of ERB used, other materials extending the function of the described composition can be added including aggregation agents, adsorbents, absorbents, germicides, germistats, or combinations thereof. An exemplary covering material for this application is photodegradable or biodegradable, as described above. As will be appreciated by those of skill in the art, the compositions used in ERBs represented in FIGS. 6a and 6b could be located along the bank of other bodies of water without departing from the scope of this disclosure.

Figure 7:
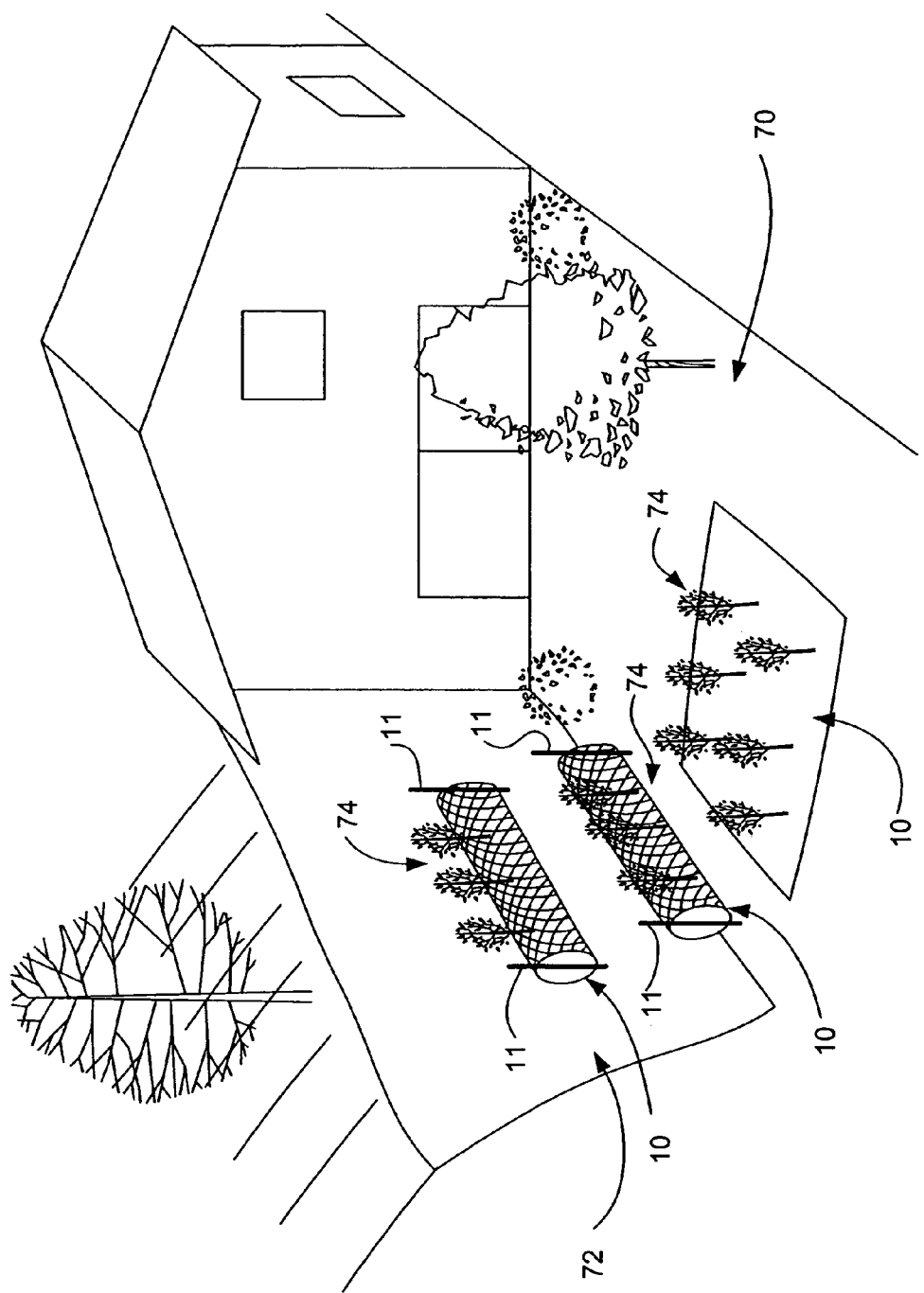
FIG. 7; is the depiction of the home garden use of a fiber roll including erosion control and revegetation.

FIG. 7 depicts the of use of the disclosed compositions in fiber rolls 10 and mats 20 for home garden use. Backyard 70, bounded on one side by sloping hillside 72 is shown using fiber rolls 10 installed on the sloping hillside 72 using stakes 11, while a mat is shown in backyard 70. Plants 74 are shown to be growing out of the fiber rolls 10 and the blanket 20. In addition to any of the embodiments of the disclosed compositions described above, plant material may be added, so that an additional function served is revegetation. Examples of suitable plant material include one or more of seeds, bulbs, rhizomes, cuttings, and seedlings. An exemplary covering material for this application is photodegradable or biodegradable, or combinations thereof, as previously described. As will be appreciated by those of skill in the art, while this embodiment is described in terms multifunctional application for home use, other types of residential, industrial, recreational, and agricultural settings can be treated using revegetation without departing from the scope of what is disclosed herein. For instance, the multifunctional compositions used for revegetation can also be used in forests, golf courses, waterways, and on embankments abutting roadways, etc.

What is claimed:

1. A device for run-off treatment and sediment retention of water comprising:
   (a) a fiber material;
   (b) one or more coagulation and/or flocculation agents selected from the group consisting of exoskeletons of anthropods and aquatic shells; and
   (c) further comprising one or more coagulation and/or flocculation agents selected from the group consisting of chitosan, conchiolin, polyacrylamide, polyamine and polydadmac.

2. The device of claim 1, further comprising a binding agent, which binds the fiber material and the one or more coagulation and/or flocculation agents.

3. The device of claim 2, wherein the binding agent binds the fiber material and the flocculation and/or coagulation agents through chemical and/or physical bonds.

4. The device of claim 1, wherein the fiber material is natural fiber material.

5. The device of claim 1, further comprising one or more coagulation and/or flocculation agents selected from the group consisting of a polymer material, a mineral, a clay, and an inorganic compound.

6. The device of claim 1, wherein the one or more coagulation and/or flocculation agents include a polymer material in a crystalline form.

7. The device of claim 1, wherein the one or more coagulation and/or flocculation agents are made up of particles of less than 10 mm in diameter.

8. The device of claim 1, wherein the one or more coagulation and/or flocculation agents are impregnated into the fiber.

9. The device of claim 1, wherein aquatic shells and the exoskeleton of anthropods are provided in said fiber material in order to retain the run-off material in the water on the said fiber material.

10. The device of claim 1, wherein the fiber material is selected from the group consisting of natural fiber, rice straw, cotton, wool, silk, coir, flax, jute, sisal, kenaf, ramie, bagasse, hemp, wheat straw, barley straw, oat straw, processed fiber, linen, paper, cardboard, paperboard, carbon impregnated paper, natural filaments, polyamides, polyacrylates, polyesters, polyacrylamides, rayon and cellulose acetate.

11. A device for treatment of run-off water and sediment retention comprising:
- a container formed in the shape of a tube;
- said container comprising a mesh;
- a fiber material packed into said tube;
- a coagulation and/or flocculation agent provided in the container and associated with the fiber material which acts to retain run-off materials in the water and/or retain sediment;
- said coagulation and/or flocculation agent is at least consisting of aquatic shells and /or the exoskeletons of anthropods; and
- further comprising a coagulation and/or flocculation agent selected from the group consisting of chitosan, conchiolin, polyacrylamide, polyamine and polydadmac.

* * * * *